United States Patent
Sorokin et al.

(10) Patent No.: US 11,370,797 B2
(45) Date of Patent: Jun. 28, 2022

(54) ANTI-VIRAL DRUG

(71) Applicant: DORING INTERNATIONAL GMBH, Oberterzen (CH)

(72) Inventors: Pavel Vladimirovich Sorokin, Novouralsk (RU); David Edmund Thorne, Oberterzen (CH)

(73) Assignee: DORING INTERNATIONAL GMBH, Oberterzen (CH)

( * ) Notice: Subject to any disclaimer, the term of this patent is extended or adjusted under 35 U.S.C. 154(b) by 0 days.

(21) Appl. No.: 16/862,290

(22) Filed: Apr. 29, 2020

(65) Prior Publication Data

US 2020/0325143 A1    Oct. 15, 2020

Related U.S. Application Data

(63) Continuation of application No. 16/079,954, filed as application No. PCT/EP2017/054423 on Feb. 24, 2017, now abandoned.

(30) Foreign Application Priority Data

Feb. 24, 2016  (EP) .................................... 16157238

(51) Int. Cl.
  *C07D 487/04*    (2006.01)
(52) U.S. Cl.
  CPC .................................. *C07D 487/04* (2013.01)
(58) Field of Classification Search
  None
  See application file for complete search history.

(56) References Cited

FOREIGN PATENT DOCUMENTS

| RU | 2 294 936 C1 | 3/2007 |
| RU | 2 343 154 C2 | 1/2009 |
| RU | 2 444 363 C2 | 3/2012 |
| WO | 2015/016818 A1 | 2/2015 |
| WO | 2015/065243 A1 | 5/2015 |

OTHER PUBLICATIONS

Grant & Hackh's Chemical Dictionary (5th Ed. 1987) at p. 148.*
International Search Report dated Jul. 21, 2017, issued in corresponding International Application No. PCT/EP2017/054423, filed Feb. 24, 2017, 6 pages.
Written Opinion dated Jul. 21, 2017, issued in corresponding International Application No. PCT/EP2017/054423, filed Feb. 24, 2017, 8 pages.
Schafer, S., Kolkhof, P. Failure is an option: learning from unsuccessful proof-of-concept trials. Drug Discovery Today. Nov. 2008, 13, 913-916.
Hörig, H., Pullman, W. From bench to clinic and back: Perspective on the 1st IQPC Translational Research conference. Journal of Translational Medicine. Dec. 2004, 2, 44.

\* cited by examiner

*Primary Examiner* — Po-Chih Chen
(74) *Attorney, Agent, or Firm* — Christensen O'Connor Johnson Kindness PLLC

(57) ABSTRACT

7-Thio-substituted-3-nitro-1,2,4-triazolo [5,1-c]-1,2,4-triazin-4(1H)-one antiviral compounds, methods their preparation, and methods of their use in the treatment of positive-sense, single-stranded RNA virus infections different from the West Nile Fever virus infections are disclosed.

7 Claims, No Drawings

ANTI-VIRAL DRUG

CROSS-REFERENCES TO RELATED APPLICATIONS

This application is a continuation of U.S. patent application Ser. No. 16/079,954, filed Aug. 24, 2018, which is a U.S. National Stage of International Application No. PCT/EP2017/054423, filed Feb. 24, 2017, which claims priority to European Application No. 16157238.3, filed Feb. 24, 2016, the disclosures of which are hereby expressly incorporated by reference in their entirety.

FIELD

The present invention relates to 7-thio-substituted-3-nitro-1,2,4-triazolo [5,1-c]-1,2,4-triazin-4(1H)-one compounds for use in the treatment of positive-sense, single-stranded RNA [herein after ssRNA] virus infections, ssRNA viruses different from the West Nile Fever virus, in particular belonging to the Coronaviridae family and methods for treating said ssRNA viruses. The present invention further relates to methods for manufacturing of said 7-thio-substituted-3-nitro-1,2,4-triazolo [5,1-c]-1,2,4-triazin-4(1H)-one compounds.

BACKGROUND

Positive-sense, single-stranded RNA viruses (ssRNA), such as ssRNA viruses belonging to the Orders Nidovirales, in particular the Coronaviridae family and the Arteriviridae family, Picornavirales, in particular the Picornaviridae family, Tymovirales and some other ssRNA viruses belonging to unassigned families such as notably the Flaviviridae family, in particular the Zika virus, the Astroviridae family, the Caliciviridae family, and the Togaviridae family cause many diseases in wildlife, domestic animals and humans. These ssRNA viruses belonging to different Orders are genetically and antigenically diverse, exhibiting broad tissue tropisms and a wide pathogenic potential.

For example, human coronaviruses belonging to the Order Nidovirales specifically to the family Coronaviridae, were first identified in the mid-1960s. The six coronaviruses that can infect people are: alpha coronaviruses 229E and NL63, and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS).

There are many coronaviruses that naturally infect animals. Most of these usually infect only one animal species or, at most, a small number of closely related species, but not people.

However, SARS-CoV can infect people and animals, including monkeys, Himalayan palm civets, raccoon dogs, cats, dogs, and rodents. MERS-CoV has also been found to infect people and animals, including camels and bats.

The epidemic of Severe Acute Respiratory Syndrome (SARS) appears to have started in Guangdong Province, China in November 2002 and spread therefrom to rapidly infect individuals in some countries around the world including Hongkong, Singapore, Vietnam, Canada, and the U.S.A., with more than 8,000 known infected cases and more than about 800 deaths worldwide (Du et al. in *Nat Rev Microbiol* 2009 Mar. 7(3): 226-236). When infected with SARS coronavirus, patients suffer from symptoms including fever, cough, dyspnea, atypical pneumonia, etc.

Middle East Respiratory Syndrome (MERS) is a viral respiratory illness that was first reported in Saudi Arabia in 2012 and has since spread to several other countries, including the United States. Most people infected with MERS-CoV developed severe acute respiratory illness, including fever, cough, and shortness of breath. Many of them have died.

Another example of a positive sense single-stranded RNA envelope virus is the flavivirus such as the tick-borne encephalitis virus (TBEV) which is associated with tick-borne encephalitis (TBE) and the Zika Virus.

The Zika virus was first isolated in 1947 and is known to cause Zika fever. As of early 2016, the most widespread outbreak of Zika fever was ongoing primarily in the Americas. People infected with the Zika virus often show no or only mild symptoms, similar to a mild form of dengue fever. However, in pregnant women the infection has a suspected link with newborn microcephaly by mother-to-child transmission.

Thus, there remains a need for antiviral compounds which are effective for use in the treatment of the ssRNA virus infections different from the West Nile Fever virus infections, in particular in the treatment of virus infections caused by ssRNA viruses belonging to the Orders Nidovirales, in particular the Coronaviridae family.

SUMMARY

Thus, the primary object of the present invention is an antiviral compound for use in the treatment of positive-sense, single-stranded RNA (herein after ssRNA] virus infections different from the West Nile Fever virus infections wherein said antiviral compound is of general formula (I) [antiviral compound (A), herein after] or a pharmaceutically acceptable salt thereof formula (I)

wherein $R^1$ is selected from an alkyl group having 1 to 12 carbon atoms which is optionally substituted by a halogen atom or hydroxyl group, a cycloalkyl group having 3 to 12 carbon atoms which is optionally substituted by a halogen atom or hydroxyl group, an aryl group, an alkylaryl group, or a cycloheteroalkyl group having 3 to 12 carbon atoms.

It is a further object of the present invention to provide methods for manufacturing said antiviral compound (A) or the pharmaceutically acceptable salt thereof.

It is also a further object of the present invention to provide methods for treating said ssRNA viruses infections different from the West Nile Fever virus infections, as mentioned above, by using the antiviral compound (A) or the pharmaceutically acceptable salt thereof.

It is also a further object of the present invention to provide pharmaceutical compositions comprising said antiviral compound (A) or the pharmaceutically acceptable salt thereof.

Antiviral Compound (A) and Pharmaceutically Acceptable Salt Thereof

As used herein the term "alkyl" has the broadest meaning generally understood in the art, and may include a moiety which is linear, branched or a combination thereof.

As used herein the term "cycloalkyl group having 3 to 12 carbon atoms" is a non-aromatic carbon-based ring composed of at least three carbon atoms and at most 12 carbon atoms. Examples of cycloalkyl group having 3 to 12 carbon atoms include, but are not limited to, cyclopropyl, cyclobutyl, cyclopentyl, cyclohexyl, etc.

As used herein the term "aryl group" is any carbon-based aromatic group including, but not limited to, phenyl, tolyl, xylyl, cumenyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. Examples of heteroaryl groups include, but are not limited to, furyl, thienyl, pyrrolyl, imidazolyl, pyridyl, pyrazyl, pyrimidinyl, indolyl, carbazolyl, isoxazolyl, isothiazolyl etc. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

As used herein the term "alkylaryl group" refers preferably to an alkylaryl group having 6 to 20 carbon atoms such as, but not limited to, benzyl, phenethyl, naphthylmethyl, optionally substituted with one or more groups including, but not limited to, alkyl, alkynyl, alkenyl, aryl, halide, nitro, amino, ester, ketone, aldehyde, hydroxy, carboxylic acid, or alkoxy.

As used herein the term "heterocycloalkyl group having 3 to 12 carbon atoms" is a cycloalkyl group as defined above where at least one of the carbon atoms of the ring is substituted with a heteroatom such as, but not limited to, nitrogen, oxygen, sulphur, or phosphorus. Examples of heterocycloalkyl groups having 3 to 12 carbon atoms include, but are not limited to, morpholine, a piperidine, n-methyl-piperazine etc.

Preferably, $R^1$ in the antiviral compound (A) or the pharmaceutically acceptable salt thereof, is selected from an alkyl group having 1 to 8 carbon atoms optionally substituted by a halogen atom or hydroxyl group, a cycloalkyl group having 3 to 6 carbon atoms which is optionally substituted by a halogen atom or hydroxyl group, a phenyl, a benzyl, a morpholine, or an imidazolyl. More preferably, $R^1$ is selected from an alkyl group having 1 to 4 carbon atoms, a cyclohexyl, a phenyl or a benzyl. Even more preferably $R^1$ is selected from methyl, ethyl, propyl or isopropyl. Most preferably, $R^1$ is a methyl group.

The antiviral compound (A), as detailed above and the pharmaceutically acceptable salts thereof, are capable of suppressing the propagation of ssRNA viruses different from the West Nile Fever virus and thus can treat or prevent these ssRNA viruses infections different from the West Nile Fever virus infections.

According to certain embodiments of the present invention, the ssRNA viruses different from the West Nile Fever virus are advantageously chosen among the ssRNA viruses belonging to the Orders Nidovirales, Picornavirales or Tymovirales or among ssRNA viruses belonging to the unassigned families selected from the group consisting of Flaviviridae, Astroviridae, Caliciviridae, and Togaviridae, preferably the Order Nidovirales.

According to a preferred embodiment of the present invention, the ssRNA viruses different from the West Nile Fever virus are selected from the group of ssRNA viruses belonging to the Coronaviridae, Arteriviridae, or Picornaviridae families, preferably belonging to the Coronaviridae family.

According to a more preferred embodiment of the present invention, the ssRNA virus is a coronavirus selected from the group consisting of an alpha coronavirus, a beta coronavirus, a gamma coronavirus or a delta coronavirus, more preferably a beta coronavirus, even more preferably a SARS-CoV or a MERS-CoV.

Thus, the antiviral compound (A), as detailed above and the pharmaceutically acceptable salts thereof are particularly effective against the coronaviruses, as mentioned above, and in particular against SARS-CoV and MERS-CoV.

According to another embodiment of the present invention, the ssRNA virus is an Arterivirus selected from the group consisting of an Equine arteritis virus, a Porcine reproductive and respiratory syndrome virus or a Simian hemorrhagic fever virus.

According to another embodiment of the present invention, the ssRNA viruses different from the West Nile Fever virus are chosen among ssRNA viruses belonging to the unassigned families selected from the group consisting of Flaviviridae, Astroviridae, Caliciviridae, and Togaviridae.

According to one embodiment of the present invention, the ssRNA viruses different from the West Nile Fever virus are chosen among ssRNA viruses belonging to the family Flaviviridae selected from the group consisting of a Flavivirus, a Hepacivirus, a Pegivirus or a Pestivirus, preferably a Flavivirus.

The Flavivirus is preferably selected from the group consisting of a Zika virus, a Tick-borne encephalitis virus, more preferably a Zika virus.

According to certain embodiments, the Hepacivirus is preferably selected from the group consisting of a Hepatitis C virus, a Hepatitis GB virus B, more preferably a Hepatitis C virus (HCV).

According to certain embodiments, the Pestivirus is preferably selected from the group consisting of a Bovine diarrhea virus 1, a Bovine diarrhea virus 2, a Border disease virus or a Classical swine fever virus, more preferably a Classical swine fever virus (CSFV).

In the present invention, the pharmaceutically acceptable salts of the antiviral compound (A), as detailed above, are not limited provided that they are capable of treating or preventing the above-mentioned specific ssRNA viruses infections.

In a preferred embodiment of the present invention, the antiviral compound (A), as detailed above, is in the form of a pharmaceutically acceptable salt.

It is understood that the antiviral compound (A), as detailed above, possessing a sufficiently acid function generally includes the corresponding pharmaceutically acceptable salts of inorganic bases and organic bases.

Therefore, in the present invention the term "pharmaceutically acceptable salts" refers to salts prepared from pharmaceutically acceptable non-toxic bases including inorganic bases and organic bases. Salts derived from nonorganic bases notably include sodium, potassium, lithium, ammonia, calcium, magnesium, ferrous, zinc, manganous, aluminum, ferric, manganic salts and the like, sodium is especially preferred. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like, arginine and lysine are especially preferred.

It is further understood that said pharmaceutically acceptable salts of antiviral compound (A) may be in the form of a solvate. Among solvates mention may be notably made of hydrates.

The term "solvate" is intended to refer to a crystal structure incorporating either stoichiometric or non-stoichiometric amounts of solvent. In case the solvate is a hydrate, said solvent is water.

For example, when the pharmaceutically acceptable salts of antiviral compound (A) are produced in a mixture of water and an organic solvent miscible with water, said pharmaceutically acceptable salts of antiviral compound (A) are produced in the form of a hydrate.

Methods to Manufacture the Antiviral Compound (A) or the Pharmaceutically Acceptable Salt Thereof Improved methods to manufacture the antiviral compound (A) or the pharmaceutically acceptable salt thereof are also an aspect of the present invention.

The antiviral compound (A) or the pharmaceutically acceptable salt thereof of the present invention can be prepared by a variety of methods known in the art. Known methods are notably described by V. L. Rusinov et al. in *Pharmaceutical Chemistry Journal*, September 1990, Volume 24, Issue 9, pp 646-650, Russian Pat. Nos. 2294936 and 2536874 and WO 2015065243 A1, the whole content of said references are herein incorporated by reference.

In these methods, the antiviral compound (A) or the pharmaceutically acceptable salt thereof, is prepared starting from 5-amino-3-methylthio-1,2,4-triazole which is subjected to a diazotization step thereby forming a diazonium salt, followed by an aza-coupling of said diazonium salt with α-nitroesters, in particular ethyl-nitroacetate. The latter compound is known to be obtained only in low yields. It is generally prepared by the nitration of acetoacetic ester with acetyl nitrate in low yield from 27 to 47% (Journal of the Chemical Society, 1958, p.2276-82 and Bulletin de la Societe Chimique de France, 31, 847-854; 1904). Thus, this synthesis suffers from having low yields and the explosiveness of acetyl nitrate.

Known methods to prepare 5-amino-3-methylthio-1,2,4-triazole are notably described by A. V. Dolzhenko et al., in Heterocycles, 2007, volume. 71, No. 2, pages 429-436, compound, and by S M Desenko et al. in Folio: Kharkov, 1998, pages 122-123.

One of the drawbacks of these known methods is the synthesis of the 5-amino-3-methylthio-1,2,4-triazole, the key precursor of 3-methylthio-1,2,4-triazol-5-yl-diazonium. In the method described by A. V. Dolzhenko et al., the synthesis of 5-amino-3-methylthio-1,2,4-triazole involves the use of the toxic carbon disulphide ($CS_2$) and the formation of an unstable cyanamide intermediate compound. In the method described by S M Desenko, the synthesis of 5-amino-3-methylthio-1,2,4-triazole involves the alkylation of 5-amino-3-mercapto-1,2,4-triazole with methyl iodide. Low yields of the key intermediate in the alkylation step are the disadvantage of this latter method.

In view of the above, there is thus a need for improved methods to manufacture the antiviral compound (A) or the pharmaceutically acceptable salt thereof, as detailed above.

It has now been found new processes for the manufacture of the antiviral compound (A) or the pharmaceutically acceptable salt thereof which allows for improved yield, high efficiency and lower manufacturing cost in particular compared to the known processes whereby 5-amino-3-methylthio-1,2,4-triazole is used as starting material.

The invention consequently relates to a process for the manufacture of the antiviral compound (A) of general formula (I) or a pharmaceutically acceptable salt thereof

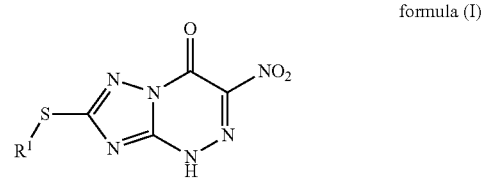

formula (I)

wherein $R^1$ is selected from an alkyl group having 1 to 12 carbon atoms which is optionally substituted by a halogen atom or hydroxyl group, a cycloalkyl group having 3 to 12 carbon atoms which is optionally substituted by a halogen atom or a hydroxyl group, an aryl group, an alkylaryl group, or a cycloheteroalkyl group having 3 to 12 carbon atoms, which comprises the steps of:

Step 1.: diazotization of a compound (B) of general formula (II):

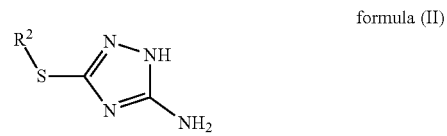

formula (II)

wherein $R^2$ is selected from hydrogen or $R^2$ has the same meaning as $R^1$, as defined here above, thereby forming a diazonium compound of general formula (III) or a pharmaceutically acceptable salt thereof:

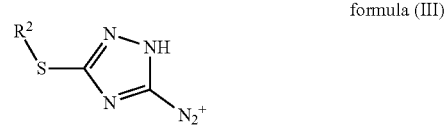

formula (III)

wherein $R^2$ has the same meaning as defined hereabove,

Step 2.: condensation reaction of the diazonium compound of general formula (III) or a pharmaceutically acceptable salt thereof, as obtained in Step 1, with at least one α-nitroester of general formula (IV), as shown below,

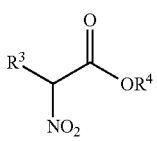

formula (IV)

wherein
R³ is independently selected from a group consisting of:
—(CO)—OR⁵ wherein R⁵ is hydrogen or an alkyl group having 1 to 24 carbon atoms which is optionally substituted by a hydroxyl group, an amine group, a halogen atom, an aryl group or an aralkyl group;
—CO)—R⁶ wherein R⁶ is an alkyl group having 1 to 12 carbon atoms which is optionally substituted by a hydroxyl group, an amine group, a halogen atom, an aryl group or an aralkyl group,
—O—(CO)—Y wherein Y is an alkyl group having 1 to 12 carbon atoms which is optionally substituted by a hydroxyl group, an amine group, a halogen atom, an aryl group or an aralkyl group;
R⁴ is an alkyl group having 1 to 24 carbon atoms which is optionally substituted by a halogen atom, an aryl group or an aralkyl group; an alkenyl group It is further understood that all definitions and preferences, as described above, equally apply for the process for the manufacture of the antiviral compound (A) of general formula (I) or a pharmaceutically acceptable salt thereof, as detailed above and equally apply for all further embodiments, as described below.

Preferably, R⁴ is an alkyl group having 1 to 12 carbon atoms which is optionally substituted by a hydroxyl group, an amine group, a halogen atom, an aryl group or an aralkyl group, more preferably R⁴ is an alkyl group having 1 to 8 carbon atoms which is optionally substituted by a hydroxyl group, an amine group, a halogen atom, an aryl group or an aralkyl group, more preferably an alkyl group having 1 to 6 carbon atoms, even more preferably an alkyl group having 1 to 4 carbon atoms. Most preferably, R⁴ is chosen among methyl, ethyl, propyl or isopropyl.

Preferably, R⁵ is an alkyl group having 1 to 12 carbon atoms which is optionally substituted by a hydroxyl group, an amine group, a halogen atom, an aryl group or an aralkyl group, more preferably R⁵ is an alkyl group having 1 to 8 carbon atoms which is optionally substituted by a hydroxyl group, an amine group, a halogen atom, an aryl group or an aralkyl group, more preferably an alkyl group having 1 to 6 carbon atoms, even more preferably an alkyl group having 1 to 4 carbon atoms. Most preferably, R⁵ is chosen among methyl, ethyl, propyl or isopropyl.

Preferably, R⁶ is an alkyl group having 1 to 8 carbon atoms which is optionally substituted by a hydroxyl group, an amine group, a halogen atom, an aryl group or an aralkyl group, more preferably R⁶ is an alkyl group having 1 to 6 carbon atoms, even more preferably an alkyl group having 1 to 4 carbon atoms. Most preferably, R⁶ is chosen among methyl, ethyl, propyl or isopropyl.

Preferably, Y is an alkyl group having 1 to 8 carbon atoms which is optionally substituted by a hydroxyl group, an amine group, a halogen atom, an aryl group or an aralkyl group, more preferably is an alkyl group having 1 to 6 carbon atoms, even more preferably an alkyl group having 1 to 4 carbon atoms. Most preferably, Y is chosen among methyl, ethyl, propyl or isopropyl.

Preferred α-nitroester of general formula (IV), as detailed above, suitable to be used in the condensation reaction of the diazonium compound of general formula (III) or a pharmaceutically acceptable salt thereof are dimethyl nitromalonate, diethyl nitromalonate, dipropyl nitromalonate, diisopropyl nitromalonate, dibutyl nitromalonate, diisobutyl nitromalonate, di-sec-butyl nitromalonate, di-tert-butyl nitromalonate, 2-nitro-methylacetoacetate, 2-nitro-ethylacetoacetate, 2-nitro-propylacetoacetate, 2-nitro-isopropylacetoacetate, 2-nitro-butylacetoacetate, 2-nitro-isobutylacetoacetate, 2-nitro-sec-butylacetoacetate, 2-nitro-tert-butylacetoacetate, more preferably dimethyl nitromalonate, diethyl nitromalonate, 2-nitro-methylacetoacetate, 2-nitro-ethylacetoacetate.

According to certain embodiments in the process of the present invention, R² is a hydrogen and the α-nitroester is having the general formula (IV), as shown below,

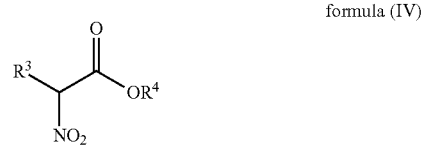

formula (IV)

wherein R³ is —(CO)—OR⁵ wherein R⁵ is an alkyl group having 1 to 24 carbon atoms which is optionally substituted by a hydroxyl group, an amine group, a halogen atom, an aryl group or an aralkyl group, preferably R⁵ is an alkyl group having 1 to 12 carbon atoms which is optionally substituted by a hydroxyl group, an amine group, a halogen atom, an aryl group or an aralkyl group, more preferably R⁵ is an alkyl group having 1 to 8 carbon atoms which is optionally substituted by a hydroxyl group, an amine group, a halogen atom, an aryl group or an aralkyl group, more preferably an alkyl group having 1 to 6 carbon atoms, even more preferably an alkyl group having 1 to 4 carbon atoms. Even more preferably, R⁵ is methyl, ethyl, propyl or isopropyl. Most preferably, R⁵ is ethyl.

According to certain embodiments in the process of the present invention, R² is equal to R¹, as defined here above, and the α-nitroester is having the general formula (IV), as shown below,

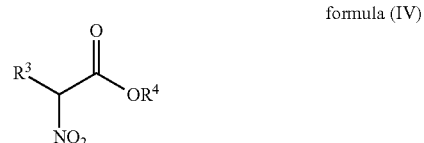

formula (IV)

wherein R³ is —(CO)—R⁶ wherein R⁶ is an alkyl group having 1 to 12 carbon atoms which is optionally substituted by a hydroxyl group, an amine group, a halogen atom, an aryl group or an aralkyl group, preferably R⁶ is an alkyl group having 1 to 8 carbon atoms which is optionally substituted by a hydroxyl group, an amine group, a halogen atom, an aryl group or an aralkyl group, more preferably R⁶ is an alkyl group having 1 to 6 carbon atoms, even more preferably an alkyl group having 1 to 4 carbon atoms, even more preferably R⁶ is methyl, ethyl, propyl or isopropyl, most preferably methyl.

The diazotization of the compound (B) of general formula (II), as detailed above, can be performed by means of diazotization methods that are known to a person skilled in the art, preferably by using sodium nitrite ($NaNO_2$) or nitrosylsulfuric acid ($HNO_5S$) in acidic medium using inorganic acids such as hydrochloric acid, sulfuric acid or phosphoric acid or mixtures thereof or organic acids such as acetic acid, trifluoroacetic acid or propionic acid or mixtures thereof. Also mixtures of inorganic acid with organic acids can be advantageously used.

Generally, the diazotization of the compound (B) of general formula (II), as detailed above, is carried out at a temperature equal to or higher than −25° C., preferably equal to or higher than −20° C., more preferably equal to or higher than −15° C. It is generally carried out at a temperature equal to or lower than 15° C., preferably at a temperature equal to or lower than 10° C., more preferably a temperature equal to or lower than 5° C. A temperature ranging from −10° C. to 5° C. is most preferred.

If desired, aqueous solutions of sodium nitrite ($NaNO_2$) or nitrosylsulfuric acid ($HNO_5S$), in particular an aqueous solution of sodium nitrite ($NaNO_2$) can be used in the form of crushed ice.

It should be mentioned that the use of such a "cold" diazotization method, as described above, advantageously ensures the safety of the process of the present invention thereby preventing an uncontrolled process of foam formation with possible subsequent detonation due to increased pressure in the system, e.g. formation of the foam—the loss of substance—disintegration of nitrogen-containing matter.

In the condensation reaction of the diazonium compound of general formula (III) or a pharmaceutically acceptable salt thereof with at least one α-nitroester of general formula (IV), as detailed above, according to Step 2. of the process of the present invention, the molar ratio of the diazonium compound of general formula (III), as detailed above, to the α-nitroester of general formula (IV), as detailed above, is advantageously from 0.5:2 to 2:0.5, preferably from 0.7:1.5 to 1.5:0.7, and more preferably from 0.8:1.2 to 1.2:0.8, even more preferably 0.9:1 to 1:0.9. Most preferably, the molar ratio is about 1:1.

According to one embodiment, the condensation reaction in Step 2. of the diazonium compound of general formula (III) or a pharmaceutically acceptable salt thereof, with the at least one α-nitroester of general formula (IV), as detailed above, is carried out in the presence of at least one pharmaceutically acceptable non-toxic inorganic or organic base.

Typical examples of said pharmaceutically acceptable non-toxic inorganic bases may include alkali metal hydroxides such as sodium hydroxide, potassium hydroxide, lithium hydroxide; alkaline earth metal hydroxides such as calcium hydroxide, magnesium hydroxide; basic alkali metal salts such as sodium carbonate, sodium hydrogencarbonate, potassium carbonate and potassium hydrogencarbonate; ammoniac. Preferred pharmaceutically acceptable non-toxic inorganic bases are sodium hydroxide and potassium hydroxide. Most preferred pharmaceutically acceptable non-toxic inorganic base is sodium hydroxide.

Typical examples of said pharmaceutically acceptable non-toxic organic bases may include primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like. Preferred pharmaceutically acceptable non-toxic organic bases are arginine and lysine. Most preferred pharmaceutically acceptable non-toxic organic base is arginine.

The amount of said pharmaceutically acceptable non-toxic inorganic or organic bases are selected as such that the reaction mixture reaches a pH of between 6.0 to 12.0, preferably between 7.0 to 11.0, more preferably between 7.5 and 10.5.

The manner of addition of said pharmaceutically acceptable non-toxic inorganic or organic bases in Step 2. is selected as such that the temperature of the reaction mixture remains below 10° C., preferably below 5° C.

Generally, the condensation of the diazonium compound of general formula (III), as detailed above, to the at least one α-nitroester of general formula (IV), as detailed above, is carried out at a temperature equal to or lower than 15° C., preferably equal to or lower than 10° C., more preferably equal to or lower than 5° C. It is generally carried out at a temperature equal to or higher than −25° C., preferably at a temperature equal to or higher than −15° C., more preferably a temperature equal to or higher than −10° C. A temperature ranging from −10° C. to 5° C. is most preferred.

If desired, the at least one α-nitroester of general formula (IV), as detailed above, can be used in combination with a solvent selected from an alcohol such as methanol, ethanol, n-propyl alcohol, isopropyl alcohol, tert-butyl alcohol, n-butyl alcohol, iso-butyl alcohol and the like; an ether such as dimethylether, diethylether, dipropylether, diisopropylether, di-tert-butylether, diisobutylether, dibutylether, di-sec-butylether, dioxane, tetrahydrofuran, dimethoxymethane, dimethoxyethane, dimethoxypropane and the like; a ketone such as dimethylketone, diethylketone, dipropylketone, methylethylketone and the like; a sulfur-containing solvent such as dimethylsulfoxide, dimethylsulfone, diphenylsulfone, diethylsulfoxide, diethylsulfone, diisopropylsulfone, tetrahydrothiophene-1,1-dioxide (commonly called tetramethylene sulfone or sulfolane), tetrahydrothiophene-1-monoxide and the like; a nitrogen-containing polar aprotic solvent such as dimethylacetamide, dimethylformamide and N-methyl pyrrolidinone (i.e., NMP) and the like; and mixtures thereof.

If appropriate, the solvent is generally used in excess. Advantageously the solvent is used in more than a thenfold excess, preferably more than a fifteenfold excess relative to the amount of the at least one α-nitroester of general formula (IV), as detailed above.

If desired, the alcohol can be applied in the form of an aqueous alcoholic solution, an organic solvent or in combination with at least one alkali metal alkoxide.

Typical examples of alkali metal alkoxides notably include but not limited to sodium methoxide, sodium isopropoxide, potassium ethoxide and the like.

For the purpose of the present invention, the term "alcoholic solution" refers to solutions of an alcohol in water, in salt water or in any other aqueous mineral salt solution.

When $R^2$ is a hydrogen then 7-mercapto-3-nitro-1,2,4-triazolo[5,1-c]-1,2,4-triazin-4(1H)-one or a pharmaceutically acceptable salt thereof is formed in Step 2. of the process for the manufacture of the antiviral compound (A) of general formula (I) or a pharmaceutically acceptable salt thereof.

According to this embodiment in the process of the present invention, 7-mercapto-3-nitro-1,2,4-triazolo[5,1-c]-1,2,4-triazin-4(1H)-one or a pharmaceutically acceptable salt thereof, as formed in Step 2. is further subjected to an alkylation reaction with an alkylating agent of formula (V): $R^1$—X or formula (VI) $R^1$—Z wherein $R^1$ has the same meaning as defined here above, X is a halogen atom or an oxygen containing functional groups such as OTos and OTMS, and Z is a sulfate group (i.e., O—S(=O)$_2$—O) or a carbonate group (i.e., O—C(=O)—O), preferably a sulfate group, thereby forming the antiviral compound (A) of general formula (I) or the pharmaceutically acceptable salt thereof.

X is preferably selected from fluorine, bromine, chlorine, iodine, OTos or OTMS; more preferably X is fluorine, bromine, chlorine, or iodine, most preferably X is iodine.

Preferably, $R^1$ is selected from an alkyl group having 1 to 4 carbon atoms, a cyclohexyl, a phenyl or a benzyl and X is fluorine, bromine, chlorine, or iodine. More preferably, $R^1$ is selected from methyl, ethyl, propyl or isopropyl and X is iodine.

In another preferred aspect, $R^1$ is selected from an alkyl group having 1 to 4 carbon atoms, a cyclohexyl, a phenyl or a benzyl and Y is a sulfate group (i.e., O—S(=O)$_2$—O) or a carbonate group (i.e., O—C(=O)—O).

In another particularly preferred aspect, $R^1$ is selected from methyl, ethyl, propyl or isopropyl and Y is sulfate.

In the present invention, the pharmaceutically acceptable salt of 7-mercapto-3-nitro-1,2,4-triazolo[5,1-c]-1,2,4-triazin-4(1H)-one may be a pharmaceutically acceptable monosalt, a pharmaceutically acceptable disalt or mixtures thereof.

As used herein, the disalt form of 7-mercapto-3-nitro-1,2,4-triazolo[5,1-c]-1,2,4-triazin-4(1H)-one refers to the di-anionic form of 7-mercapto-3-nitro-1,2,4-triazolo[5,1-c]-1,2,4-triazin-4(1H)-one combined with two pharmaceutically acceptable cations, each independently from each other derived from pharmaceutically acceptable non-toxic inorganic or bases organic bases, as detailed above.

As used herein, the monosalt form of 7-mercapto-3-nitro-1,2,4-triazolo[5,1-c]-1,2,4-triazin-4(1H)-one refers to the mono-anionic form of 7-mercapto-3-nitro-1,2,4-triazolo[5,1-c]-1,2,4-triazin-4(1H)-one combined with one cation derived from pharmaceutically acceptable non-toxic inorganic or bases organic bases, as detailed above.

Pharmaceutically acceptable non-toxic inorganic cations notably include sodium, potassium, lithium, ammonia, calcium, magnesium, ferrous, zinc, manganous, aluminum, ferric, manganic cations and the like, sodium cation is especially preferred. Pharmaceutically acceptable organic non-toxic cations notably include cations of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like, arginine cation and lysine cation are especially preferred.

In a preferred embodiment of the present invention, 7-mercapto-3-nitro-1,2,4-triazolo[5,1-c]-1,2,4-triazin-4(1H)-one is in the form of the disalt, as defined above.

Generally, the alkylation of 7-mercapto-3-nitro-1,2,4-triazolo[5,1-c]-1,2,4-triazin-4(1H)-one or a monosalt or a disalt thereof, is generally carried out at ambient temperature.

The Inventors have now surprisingly found that the process for the manufacture of the antiviral compound (A) of general formula (I) or a pharmaceutically acceptable salt thereof, comprising the three steps of diazotization of 5-amino-3-mercapto-1,2,4-triazole (i.e. a compound (B) of general formula (II) having $R^2$ being a hydrogen), thereby forming 3-mercapto-1,2,4-triazol-5-yl-diazonium or a monosalt thereof, as detailed above (i.e. Step 1.), followed by condensation reaction of the 3-mercapto-1,2,4-triazol-5-yl-diazonium or the monosalt thereof with at least one α-nitroester of general formula II, as detailed above (i.e. Step 2.), subsequently followed by the alkylation of 7-mercapto-3-nitro-1,2,4-triazolo[5,1-c]-1,2,4-triazin-4(1H)-one or a monosalt or a disalt thereof, as detailed above, can be carried out without isolation of any the intermediates formed in this process according to the invention. This being said, this single-stage process according to the invention allows for improved yield, high efficiency and lower manufacturing cost in particular compared to the known multi-stage processes as notably described by V. L. Rusinov et al. in *Pharmaceutical Chemistry Journal*, September 1990, Volume 24, Issue 9, pp 646-650, and Russian Pat. Nos. 2294936 and 2536874, as mentioned above.

When $R^2$ is equal to $R^1$ as defined here above, then the antiviral compound (A) of general formula (I) or a pharmaceutically acceptable salt is formed in Step 2. of the process thereby allowing to avoid the final step of alkylation.

There is also a further need that the compound (B) of general formula (II$_{R1}$), wherein $R^2$ is equal to $R^1$, as shown below, can be easily synthesized in high yield and in a cost effective manner.

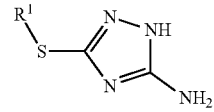

formula (II$_{R1}$)

The inventors have now surprisingly found that it is possible to provide an improved process for the manufacture of the compound (B) of general formula (II$_{R1}$) fulfilling the above mentioned needs.

Another object of the present invention is a process for the manufacture of the compound (B) of general formula (II$_{R1}$), comprising a condensation reaction of aminoguanidine with a thio compound of general formula (VII):

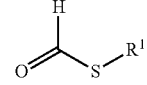

formula (VII)

wherein $R^1$ is selected from an alkyl group having 1 to 12 carbon atoms which is optionally substituted by a halogen atom or hydroxyl group, a cycloalkyl group having 3 to 12 carbon atoms which is optionally substituted by a halogen atom or hydroxyl group, an aryl group, an alkylaryl group, or a cycloheteroalkyl group having 3 to 12 carbon atoms.

The definitions and preferences described above for the process for the manufacture of the antiviral compound (A) of general formula (I) or a pharmaceutically acceptable salt thereof according to the invention equally apply to the process for the manufacture of the starting material, namely the compound (B) of general formula (II$_{R1}$).

Preferred thio compounds of general formula (VII) are chosen among S-methyl thio-formate, S-ethyl thioformate, S-propyl thioformate, S-isopropyl thioformate, S-butyl thioformate, S-isobutyl thioformate, S-sec-butyl thioformate, S-tert-butyl thioformate, S-benzyl thioformate, S-phenyl thioformate, S-cyclopropyl thioformate, S-cyclobutyl thioformate, S-cyclopentyl thioformate, S-cyclohexyl thioformate, S-methyl thio-formate is especially preferred.

The condensation reaction of aminoguanidine with the thio compound of general formula (VII), in particular methylthio-formate, may advantageously be carried out in the presence of a base. If a base is used, it may be an inorganic base or an organic base, preferably an organic base. The organic base may be selected from the group consisting of nitrogen-containing heterocyclic compounds such as pyridine, quinoline or picoline; and tertiary bases such as triethylamine, dimethylaniline, diethylaniline and 4-dimethylaminopyridine. Among them, pyridine, triethylamine, dimethylaniline, diethylaniline and 4-dimethylaminopyridine are preferred. Among them, pyridine is particularly preferred. These bases may be used alone or in combination as a mixture.

The inorganic base may be selected from the group consisting of alkali metal hydroxides such as sodium hydroxide, potassium hydroxide, lithium hydroxide, cesium hydroxide, alkaline earth metal hydroxides such as calcium hydroxide, barium hydroxide, magnesium hydroxide, strontium hydroxide, and basic alkali metal salts such as sodium carbonate, sodium hydrogencarbonate, potassium carbonate and potassium hydrogencarbonate. The preferred base is sodium hydroxide.

Pharmaceutical Composition (P)

The present invention also relates to a pharmaceutical composition [pharmaceutical composition (P), herein after] for treating or preventing ssRNA virus infections different from the West Nile Fever virus infections, as detailed above, comprising the compound (A) of general formula (I), or a pharmaceutically acceptable salt thereof, as detailed above, as an active ingredient.

It is further understood that all definitions and preferences, as described above, equally apply for the pharmaceutical composition (P) of the present invention, as detailed above.

The pharmaceutical composition (P) of the present invention may further comprise one or more pharmaceutically acceptable carriers.

Pharmaceutically acceptable carriers suitable for use in the pharmaceutical composition (P) notably include, but not limited to, fillers, expanders, binders, moisturizers, disintegrants, surfactants, lubricants, and the like The pharmaceutical composition (P) of the present invention may also further comprise one or more diluents, or one or more excipients typically used in accordance with the preparation dosage form.

The pharmaceutical composition (P) can be formulated in various forms depending on the purpose of the treatment, and representative examples are tablets, pills, pulves, liquids, suspensions, capsules, suppositories, injections (liquid, suspension, etc.), sprays, aerosols, vaporoles, sustained-release microcapsules, etc.

The pharmaceutical composition (P) of the present invention can suitably comprise the active ingredient, the compound (A) of general formula (I), or a pharmaceutically acceptable salt thereof, as detailed above, in a widely ranging proportion typically from about $1.0 \times 10^{-5}$ to about 100.0 wt. %, and preferably about $1.0 \times 10^{-4}$ to about 99.0 wt. %, relative to the total weight of the pharmaceutical composition (P). It is further understood that the proportion of the compound (A) of general formula (I), or a pharmaceutically acceptable salt thereof, is generally determined by how said pharmaceutical composition (P) is administered (e.g. in solid dosage form, liquid dosage form).

The pharmaceutical composition (P) of the present invention may also further comprise one or more additional ingredients.

Non-limiting examples of suitable additional ingredients notably include buffers, isotonizing agents, chelating agents, coloring agents, preservatives, perfumes, flavors, sweeteners, other drugs and the like.

Among buffers mention may be notably made of phosphoric acids, acetic acids, citric acids, ε-aminocaproic acids, glutamic acid and salts thereof (e.g. alkali metal salts and alkaline earth metal salts such as sodium salts, potassium salts, calcium salts, magnesium salts, etc.).

Among isotonizing agents mention may be notably made of sodium chloride, potassium chloride, saccharides, glycerol, etc.

Among chelating agents mention may be notably made of sodium edetate, citric acid, Trilon® (salt of EDTA), Unithiol ((RS)-2,3-bis(sulfanyl)propane-1-sulfonate) and etc.

In addition to use as a liquid drug, the pharmaceutical composition (P) of the present invention can also be freeze-dried for preservation, and, before use, dissolved in an aqueous buffer containing water, physiological saline or the like to give a suitable concentration.

The pharmaceutical compositions (P) of the present invention may further be prepared in solid dosage forms such as tablets, pills, pulves, powders, granules, capsules and the like, and in liquid dosage forms such as solutions, suspensions, emulsions, syrups, elixirs and the like. Such compositions can further be made into forms such as oral, parenteral, nasal, vaginal, suppository, sublingual tablet, ointment, are the like by following conventional methods for mixing, formulation and preparation.

Stated more specifically, for the formulation of tablets, the following drug carriers can be used as mentioned above: excipients such as lactose, white soft sugar, sodium chloride, glucose, urea, starch, calcium carbonate, kaolin, crystalline cellulose, silicic acid, calcium silicate, potassium phosphate, etc.; binders such as water, ethanol, propanol, simple syrups, glucose liquids, starch liquids, gelatin solutions, carboxymethylcellulose, hydroxypropylcellulose, methyl cellulose, polyvinyl pyrrolidone, etc.; disintegrators such as carboxymethylcellulose sodium, carboxymethyl cellulose calcium, low-substituted hydroxypropylcellulose, desiccation starch, sodium alginate, agar powder, laminaran powder, sodium hydrogencarbonate, calcium carbonate, crosspovidone, etc.; surfacants such as polyoxyethylene sorbitan fatty acid esters, sodium lauryl sulfate, stearic acid monoglycerides, etc.; disintegration inhibitors such as white soft sugar, stearin, cocoa butter, hydrogenated oils, etc.; absorption enhancers such as quaternary ammonium bases, sodium lauryl sulfate, etc.; humectants such as glycerin, starch, etc.; adsorbents such as starch, lactose, kaolin, bentonite, colloidal silicic acid, etc.; lubricants such as purified talc, stearates such as magnesium stearate, boric acid powder, polyethylene glycol, etc.; and the like.

Tablets can also be prepared as necessary in the form of coated tablets covered with conventional coatings or films, for example, sugar-coated tablets, gelatine film-coated tablets, enteric-coated tablets, film-coated tablets, and double- or multi-layered tablets.

For the formulation of pills, usable drug carriers are, for example, excipients such as glucose, lactose, starch, cacao butter, hardened vegetable oil, kaolin, talc, etc.; binders such as gum arabic powder, tragacanth powder, gelatin, ethanol, etc.; and disintegrators such as laminaran, agar, etc.

Capsules can be formed in conventional manners by mixing the above various drug carriers with the active ingredient of the present invention, and then filling the mixture into hard or soft gelatin or the like.

Liquid dosage forms for oral administration may contain routinely used inert diluents, for example, water-containing pharmaceutically acceptable solutions, emulsions, suspensions, syrups, elixirs, etc., and can further contain auxiliaries such as wetting agents, emulsions, suspension agents, etc. These can be prepared by conventional procedures.

Liquid dosage forms for parenteral administration, such as sterilized aqueous or non-aqueous solutions, emulsions, suspensions, etc., can be formulated by using diluents, e.g. water, ethyl alcohol, propylene glycol, polyethylene glycol, ethoxylated isostearyl alcohol, polyoxylated isostearyl alcohol, polyoxyethylene sorbitan fatty acid esters and vegetable oils such as olive oil, etc. Injectable organic esters, such as ethyl oleate, can also be admixed. Furthermore, routinely used solubilizing agents, buffers, wetting agents, emulsifiers, suspension agents, preservatives, dispersants, etc. can be added. Sterilization can be carried out by, for example, a filtration operation in which the preparation is passed through a bacterial filter; mixed with a sterilant; irradiated; heat treated and/or the like. The preparation can also be formulated in the form of a sterilizable solid composition such that it can be dissolved in sterile water or like medium suitable for sterilizing immediately before use.

For the formulation of suppository and vaginal dosage forms, usable drug carriers are, for example, polyethylene glycol, cacao butter, higher alcohols, esters of higher alcohols, gelatin, semisynthetic glyceride, etc.

The pharmaceutical compositions (P) for spray, aerosol, vaporole, nasal and sublingual dosages can be prepared using known standard excipients by following conventional methods.

The administration routes of the pharmaceutical compositions (P) of the present invention are not limited, and can be accordingly determined based on the preparation form; age, sex, other conditions of patient; severeness of symptoms, etc. For example, tablets, pills, liquids, suspensions, emulsions, granules and capsules are orally administered, and injectable forms are intravenously administered singularly or in combination with typical replacement fluids such as those containing glucose, amino acids, etc., or if necessary, can be administered as they are intramuscularly, endermically, subcutaneously or intra-abdominally. Suppositories are rectally administered, vaginal forms are vaginally administered, nasal forms are intranasally administered and sublingual forms are intraorally administered.

Dosages of the pharmaceutical compositions (P) of the present invention are not limited, and can be selected from wide ranges based accordingly to the desired treatment efficacy, administration route, treatment period, age, sex and other conditions of the patient, etc. The pharmaceutical compositions (P) is typically administered in a dose of about $1.0 \times 10^{-4}$ mg to about 9500.0 mg, preferably about $1.0 \times 10^{-3}$ mg to about 1000.0 mg, more preferably about 0.01 mg to about 500.0 mg and most preferably about 0.1 mg to about 100.0 mg, per 1 kg of body weight per day per adult in terms of the active ingredient, in one to several portions a day.

EXAMPLES

The invention will be now described in more details with reference to the following examples, whose purpose is merely illustrative and not intended to limit the scope of the invention.

Example 1: One Pot Synthesis of the Sodium Salt of 7-methylthio-3-nitro [1, 2, 4] triazolo [5,1-c] [1, 2, 4] triazin-4 (1H)-One Step 1: Diazotization of compound (B): A solution (solution [1], herein after) was prepared of 5.8 g (0.05 M) of 5-amino-3-mercapto-1,2,4-triazole in 6.7 ml of nitric acid (15 M) and 12 ml of water. Said solution [1] was refrigerated to −7° C. Then a 40% sodium nitrite solution was added to the solution [1] in portions of 0.5 mL to obtain a total amount of sodium nitrite equal to 3.8 g in the mixture.

Step 2: Condensation of diazonium compound with an α-nitroester: To the resulting diazonium salt of step 1, 8.54 ml of diethyl nitromalonate was added. After holding for five minutes, a cooled solution of sodium hydroxide was slowly added dropwise to the reaction mixture until the pH was between pH 9 and pH 10 (solution [2], herein after). The resulting solution [2] was stirred at 0° C. for 1 hour and at room temperature for 2 hours.

Step 3: alkylation: To the solution [2] of step 2, 6.23 ml (0.1 mol) of methyl iodide was added. The mixture was stirred for 1 hour at room temperature and filtered. The resulting precipitate was successively crystallized from water and dried in air. The reaction scheme is depicted below in Scheme 1.

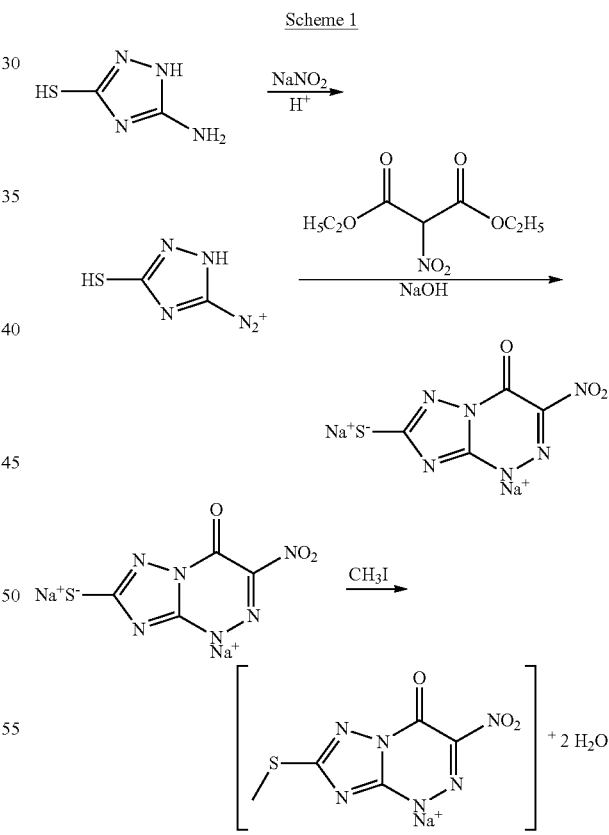

The yield was 9.87 g (69%).

Physical and chemical characteristics of the sodium salt of 7-methylthio-3-nitro [1, 2, 4] triazolo [5,1-c] [1, 2, 4] triazin-4 (1H)-one sodium salt: yellow crystalline powder, soluble in water, acetone, dimethylsulfoxide, dimethylformamide, insoluble in chloroform; $T_{melt}$=300° C., $^1$H NMR spectrum, δ, ppm, solvent DMSO-d$_6$: 2.62 (3H, s, SCH$_3$); IR spectrum, n, cm$^{-1}$: 3535 (OH), 1649 (C=O), 1505 (NO$_2$), 1367 (NO$_2$); found, %: C—20.86, H 2.51, N 29.28; C$_5$H$_7$N$_6$NaO$_5$S; Calculated, %: C—20.98, H 2.47, N 29.36.

Example 2: Synthesis of the Sodium Salt of 7-methylthio-3-nitro [1, 2, 4] triazolo [5,1-c] [1, 2, 4] triazin-4 (1H)-One Sodium Salt In this example the synthesis comprises 3 steps: in the first step 5-amino-3-mercapto-1,2,4-triazole (i.e. compound (B)) was prepared by condensation of aminoguanidine with a thio-derivative (thio ester) of formic acid, HC(=O)S'R, wherein —R was: methyl. In the second step 5-amino-3-mercapto-1,2,4-triazole was converted to the corresponding diazonium salt. In the third step this diazonium salt was reacted with an α-nitroester, 2-nitroacetoacetic ester, to form the 7-methylthio-3-nitro [1, 2, 4] triazolo [5,1-c] [1, 2, 4] triazin-4 (1H)-one. The different steps are explained in more detail below.

Step 1: Synthesis of compound (B): In a reaction flask equipped with a stirrer, reflux condenser, under inert gas (nitrogen, argon), 20 g (0.1 mol) of aminoguanidine and 7.6 g (0.1 mol) methylthio-formate was added to 400 ml of absolute pyridine. The reaction mixture was boiled for 4 hours at 115° C. Subsequently the reaction mixture was transferred into distilled water and washed several times with water. The washed mixture was dried over a Nutsche filter under vacuum. Recrystallization was carried out from ethanol. The reaction scheme is depicted below in Scheme 2.

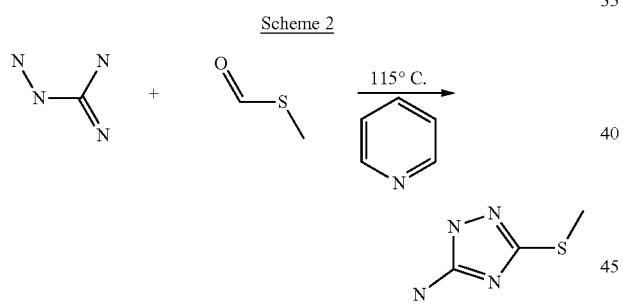

The yield was 19.3 g (70%)

Step 2: Diazotation of compound (B): A solution (solution [3], herein after) was prepared of 26 g (0.1 mol) of 5-amino-3-mercapto-1,2,4-triazole (as obtained in step 1) in 32 ml of nitric acid (0.1 mol) and 200 ml of water. The solution was mixed and cooled to −5° C. In a separate recipient, a 0.1 M solution of sodium nitrite was prepared by dissolving 16 g of sodium nitrite in 100 ml of water. The sodium nitrite solution was put in the freezer until there was ice formation and subsequently the ice was crushed. Thereafter, the solution [3] and the sodium nitrite crushed ice were transferred into a 1 L reactor and stirred for 1 hour while the reactor temperature was kept at 0° C. The low temperature and the fact that the two reaction components are in different phases (i.e. liquid and solid) ensured a slow gradual progress of diazotization reaction at the phase interface. The end of the diazotization process was controlled by a iodine starch test (proof of the absence of sodium nitrite in a free state).

The reaction scheme is depicted in Scheme 3.

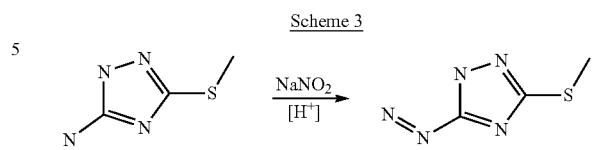

Step 3: Condensation of the diazonium compound with an α-nitroester: A solution (solution [4], herein after) was prepared by mixing 17.5 g of methyl 2-nitro-acetoacetate in 300 mL of isopropanol. The solution [4] was mixed with the diazonium salt of step 2. The mixture was cooled to 0° C. At 0° C., a 10% sodium hydroxide solution was added to the reaction mixture (to neutralize residual nitrite and acetate) until there was a marked alkaline reaction (pH between 8 and 9). The temperature was controlled and was kept below +5° C. The resulting mixture was stirred for 1 hour. The precipitate was filtered off and dried in air. The yield was 78%.

The reaction scheme is depicted in Scheme 4

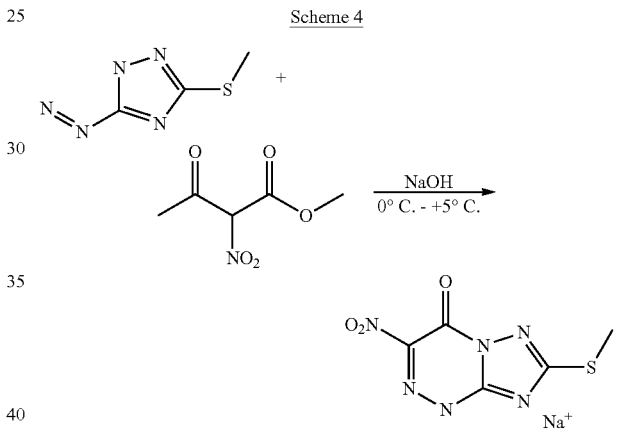

Example 3: Synthesis of the Sodium Salt of 7-methylthio-3-nitro [1, 2, 4] triazolo [5,1-c] [1, 2, 4] triazin-4 (1H)-One The synthesis of the sodium salt of 7-methylthio-3-nitro-1,2,4-triazolo [5,1-c]-1,2,4-triazin-7-one may be carried out as in Example 2, only in step 2 the aqueous alcohol solution is replaced by an alcohol with alkali (such as sodium hydroxide). The yield of the antiviral compound (A) (sodium salt of 7-methylthio-3-nitro [1 2, 4] triazolo [5,1-c] [1, 2, 4] triazin-4 (1H)-one) may increase to 83%.

The reaction scheme is depicted below in Scheme 5:

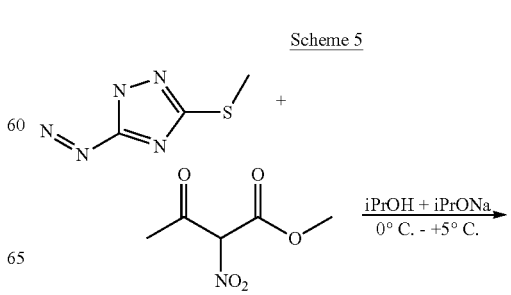

The embodiments of the invention in which an exclusive property or privilege is claimed are defined as follows:

1. A method of treatment of a virus infection caused by a positive-sense, single-stranded RNA (ssRNA) virus different from West Nile Fever virus, comprising administering a therapeutically effective amount of a compound of formula (I) or a pharmaceutically acceptable salt thereof to a subject in need thereof, formula (I)

wherein
- R¹ is an unsubstituted alkyl group having 1 to 4 carbon atoms; and
- the positive-sense, single-stranded RNA (ssRNA) virus different from the West Nile Fever virus is selected from the positive-sense, single-stranded RNA (ssRNA) virus belonging to Coronaviridae family.

2. The method of claim 1, wherein R¹ is a methyl group.

3. The method of claim 1 wherein the positive-sense, single-stranded RNA (ssRNA) virus is a coronavirus selected from the group consisting of an alpha coronavirus, a beta coronavirus, a gamma coronavirus, and a delta coronavirus.

4. The method of claim 1, wherein the positive-sense, single-stranded RNA (ssRNA) virus is a beta coronavirus.

5. The method of claim 1, wherein the positive-sense, single-stranded RNA (ssRNA) virus is a SARS-CoV or a MERS-CoV.

6. The method of claim 1, wherein administering the therapeutically effective amount of the compound of formula (I) or the pharmaceutically acceptable salt thereof further comprises: administering, with the compound of formula (I) one or more carriers selected from the group consisting of fillers, expanders, binders, moisturizers, disintegrants, surfactants, lubricants, diluents, excipients, buffers, isotonizing agents, chelating agents, coloring agents, preservatives, perfumes, flavors, sweeteners, and combinations thereof.

7. The method of claim 1, wherein the compound of formula (I) or the pharmaceutically acceptable salt thereof is administered in the form of:
- a solid dosage form selected from the group consisting of: a tablet, a pill, a pulve, a powder, a granule, and a capsule;
- a liquid dosage form selected from the group consisting of: a solution, a suspension, an emulsion, a syrup, and an elixir; or
- an ointment.

* * * * *